United States Patent
Gupta

(10) Patent No.: US 9,383,346 B2
(45) Date of Patent: Jul. 5, 2016

(54) EXPANDABLE JACKET AND ITS CALIBRATION DEVICE FOR TRIAXIAL TESTS ON SOILS

(71) Applicant: Ramesh Chandra Gupta, Ashburn, VA (US)

(72) Inventor: Ramesh Chandra Gupta, Ashburn, VA (US)

( * ) Notice: Subject to any disclaimer, the term of this patent is extended or adjusted under 35 U.S.C. 154(b) by 0 days.

(21) Appl. No.: 14/660,887

(22) Filed: Mar. 17, 2015

(65) Prior Publication Data

US 2015/0268217 A1    Sep. 24, 2015

(51) Int. Cl.
*G01N 33/24* (2006.01)
*G01N 3/08* (2006.01)

(52) U.S. Cl.
CPC . *G01N 33/24* (2013.01); *G01N 3/08* (2013.01)

(58) Field of Classification Search
CPC ........ E21B 49/006; E02D 1/022; G01N 3/08; G01N 3/00; G01N 33/24; G01N 3/10
See application file for complete search history.

(56) References Cited

U.S. PATENT DOCUMENTS

| | | | | |
|---|---|---|---|---|
| 4,122,704 | A * | 10/1978 | Lutenegger | G01N 3/10 73/822 |
| 5,226,310 | A * | 7/1993 | Steiger | E21B 49/006 73/38 |
| 6,595,068 | B2 * | 7/2003 | Brovold | G01N 3/10 73/803 |
| 6,655,220 | B1 * | 12/2003 | Reiffsteck | E02D 1/04 73/152.59 |
| 7,353,714 | B2 * | 4/2008 | England | E02D 33/00 73/784 |
| 7,520,177 | B2 * | 4/2009 | Secq | G01B 5/30 73/795 |
| 2005/0039540 | A1 * | 2/2005 | Crockford | G01L 5/0004 73/784 |
| 2015/0047418 | A1 * | 2/2015 | Gupta | G01N 3/08 73/38 |

OTHER PUBLICATIONS

USPTO.GOV, Advanced Claim Drafting, 16th Annual Independent Inventors Conference, Aug. 15-16, 2014.*
Bishop, A. W. and Green, G. E. "The influence of end restraint on the compression strength of a cohesionless soil," Geotechnique, 1965, pp. 243-266, vol. 15, UK.
Gupta, R. C. "Finite strain analysis for expansion of cavities in granular soils," Soils and Foundations, 2002 (a), pp. 105-115, vol. 42, No. 6, Tokyo, Japan.
Gupta, R. C. "Estimating bearing capacity factors and cone tip resistance," Soils and foundations, 2002(b), pp. 117-127, vol. 42, No. 6, Tokyo, Japan.
Lee, K. L. "End restraint effects on undrained static triaxial strength of sand,"Journal of Geotechnical Engineering Division,ASCE, 1978,pp. 687-703, vol. 104, New York, USA.

(Continued)

*Primary Examiner* — Michael Zarroli

(57) ABSTRACT

During triaxial compression test, a soil specimen experiences reduction of its height with increase in its diameter. New cross-sectional area is calculated assuming uniform increase in diameter. This condition is seldom met in actual soil specimens, because specimen undergoes non-uniform increase in diameter and very often with localized bulging in specimen affecting the accuracy of calculation of deviator stress, shears strength and volume change characteristics. The expandable jacket included in this invention consists of circular segmental metal plates wrapped around the soil specimen and elastomeric rubber bands or rings around the segmental plates to permit uniform radial expansion and maintain uniform diameter of the specimen during the test and thereby providing accurate values of deviator stress, volume change characteristics and shear strength of soil specimen. The calibration device for calibration of expandable jacket shall provide the magnitude of correction to be made in deviator stress.

1 Claim, 12 Drawing Sheets

(56) References Cited

OTHER PUBLICATIONS

Rochelle,P.,Leroueil,S.,Trak,B., Blais-Lerox, L.,and Tavenas, F."Observational app-roach to membrane and area corrections in triaxial tests," ASTM, STP977,1988,715-731, USA.

Rowe, P. W. and Barden, L. "Importance of free ends in triaxial testing, " Journal of Soil Mech. and Found. Division, ASCE, 1964, pp. 1-27, vol. 90, No. SM1,New York,USA.

Saada, A. S. and Townsend, F. C."Laboratory strength testing of soils, state of the art," ASTM, Special Technical Publication 740, 1981, pp. 7-77, Philadelphia, USA.

Sheng, D.,Westerberg, B.,Mattsson,H. and Axelsso,K."Effects of end restraint and strain rate in triaxial tests," Computers and Geotechnics,1997,163-182, vol. 21, Netherlands.

Vesic, A. S. (1972). "Expansion of cavities in infinite soil mass, "Journal of Soil Mechanics and Foundation Division, ASCE, 1972, pp. 265-290, vol. 98(3), New York, USA.

\* cited by examiner

EXPANDABLE JACKET AND ITS CALIBRATION DEVICE FOR TRIAXIAL TESTS ON SOILS

CROSS REFERENCE TO RELATED APPLICATIONS (IF ANY)

This specification is complete in itself.

STATEMENT OF FEDERALLY SPONSORED RESEARCH/DEVELOPMENT (IF ANY)

This invention is not sponsored or supported by federally sponsored research or development. This invention has been developed by me, Dr. Ramesh Chandra Gupta, Ph. D., P.E, President and Sole Owner of SAR6 INC., solely at my own cost and time.

THE NAMES OF THE PARTIES TO A JOINT RESEARCH AGREEMENT IF THE CLAIMED INVENTION WAS MADE AS A RESULT OF ACTIVITIES WITHIN THE SCOPE OF A JOINT RESEARCH AGREEMENT

There is no joint research agreement with anyone. As stated earlier, this research/invention was conceived and completed solely by me (Dr. Ramesh C. Gupta, the inventor). It is my individual research work for this invention.

REFERENCE TO A "SEQUENCE LISTING," A TABLE, OR COMPUTER PROGRAM LISTING APPENDIX SUBMITTED ON A COMPACTED DISC AND INCORPORATION BY REFERENCE OF THE MATERIAL ON COMPACT DISC. THE TOTAL NUMBER OF COMPACT DISC INCLUDING DUPLICATES AND THE FILES ON EACH COMPACT DISC SHALL BE SPECIFIED

List of figures and tables with figure and table captions has been included in Item 8. The whole package is submitted in PDF format attached to the email. A compact disc containing the whole package can be submitted on demand from Patent Office.

BACKGROUND OF THE INVENTION

It is claimed by the inventor (Dr. Ramesh Chandra Gupta, Ph. D., P.E.) that with the use of expandable jacket around the soil specimen, uniform increase in diameter of soil specimen shall occur through its height without any localized bulging, permitting accurate calculation of new area of cross-section at any instant of time, when axial vertical load is applied during the triaxial compression test. New area of cross-section is required to calculate the deviator stress during process of shearing at any instant of time.

The triaxial compression test is considered to simulate in-situ conditions of a soil element at any depth below the ground surface. Lateral pressure applied in the triaxial chamber is generally kept approximately equal to in-situ horizontal stress from where the soil sample is extracted. It is a standard test for determination of strength and volume change characteristics of soils, (ASTM Designation: D4767-11, ASTM Designation: D2850). When vertical load is applied to any soil element located at certain depths, the soil element experiences vertical displacement with simultaneous lateral displacement. The ratio of lateral strain with axial (vertical) strain is governed by the Poisson's ratio of soil. The soil element at deeper depths does not or cannot experience non-uniform lateral displacement or localized bulging due to lateral uniform elastic restraint provided by the adjoining soil. Volume change in soil element depends on both vertical displacement and lateral displacement. Thus any determination of volume change from triaxial compression test where soil specimen undergoes non-uniform lateral displacement, (very often with localized bulging), does not or cannot be considered to accurately represent the actual volume change of soil elements insitu with increase in the vertical load.

To solve these problems and to accurately simulate insitu conditions, an expandable jacket as explained and detailed below, is being introduced in this invention to maintain uniform cross-section of the soil specimen without any possibility of localized bulging. From the triaxial compression tests, it has been established that loose or soft soils decrease in volume and very stiff to hard or dense to very dense soil increase in volume or dilate during process of shearing, however this research is based on tests when soil specimen experienced non-uniform lateral displacement along with probable localized bulging. After eliminating non-uniform lateral displacement of the specimen by use of expandable jacket, it shall be possible to re-review or re-check or confirm whether loose or soft soils shall continue to experience decrease in volume; and dense to very dense or very stiff to hard soils shall continue to experience increase in volume (dilation) during the process of shearing in the triaxial compression tests.

BRIEF SUMMARY OF THE INVENTION

FIG. 1(a) shows the cylindrical shape of the soil specimen before beginning the triaxial compression test. FIG. 1(b) shows the barrel shape of the soil specimen with non-uniform lateral displacement during the triaxial compression test.

The expandable jacket consists of about 10 stainless steel segment plates, circular arch in shape for 2.8" (71 mm) diameter specimen as shown in FIG. 2. The plates may vary between 1/8" and 3/8" (3.2 mm and 9.53 mm) in thickness. Thicker segment plates will not bend under the force exerted by rubber bands and in this respect may have some advantage over thinner plates. These plates are installed around the membrane which covers the specimen, using two-half circular brackets as shown in FIG. 2 and FIG. 3. The thickness of these brackets can vary between 1/4" and 3/8" (6.35 mm and 9.53 mm). Rubber bands of minimum 1/8" (3.2 mm) thickness are slipped on around the plates at marked locations as shown in FIG. 4. The width of rubber bands can vary between 1/8" and 3/8" (3.2 mm and 9.53 mm). The upper and lower brackets are then un-installed. Remaining rubber bands are slipped on around the plates in the space earlier covered by the brackets, as shown in FIG. 5. The expandable jacket has thus been installed around the soil specimen. Since in the beginning of test, segmental circular plates are resting against the top and bottom porous discs, lateral load exerted by rubber bands acts on the porous discs and very little, if any, directly on the soil specimen.

Alternatively, the segment plates can be assembled around soil specimen by use of two 1" (25.4 mm) wide leather or nylon (or polyester or polypropylene) VELCRO hook-and-loop straps. First, segment plates are fastened to Velcro strap using 5-44 or M-3 screws as shown in FIG. 6. Then the assembled plates are wrapped around the soil specimen and maintained in position by VELCRO hook-and-loop strap as shown in FIG. 7. The rubber bands of minimum thickness of 1/8" (3.17 mm) are slipped on around the plates as shown in FIG. 8. The screws are unthreaded to remove the strap. The remaining rubber bands are then slipped on around the plates in the space earlier occupied by VELCRO hook-and-loop straps, as shown in FIG. 9. The expandable jacket has now been installed around the soil specimen. The other steps such as placing the chamber, filling the chamber with water and installing loading device on top platen etc. are followed as per ASTM standards or other accepted standards to perform the triaxial test.

DETAILED DESCRIPTION OF THE INVENTION

Figure 1:
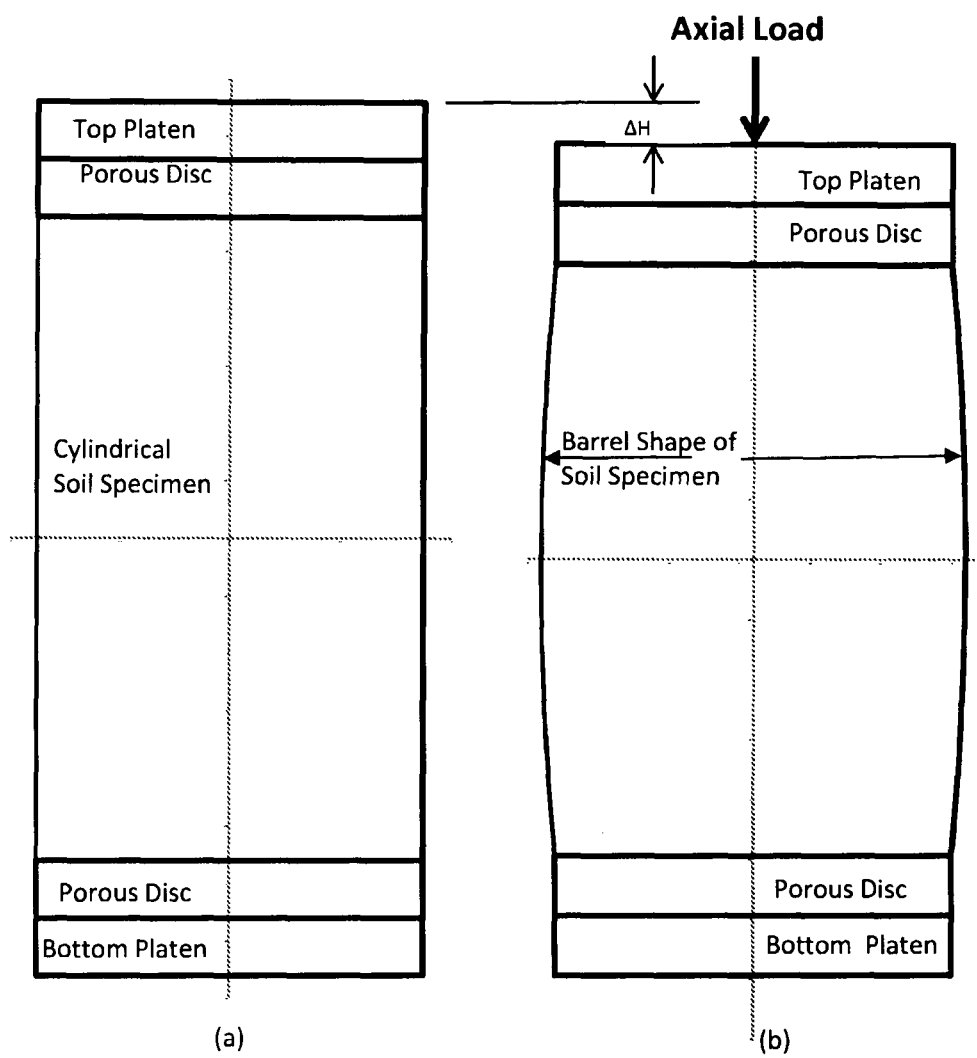
FIG. 1(a) describes the initial shape of the cylindrical soil specimen before beginning of the triaxial compression test.
FIG. 1(b) describes the barrel shape of the same specimen with non-uniform lateral displacement during the test.

Detailed description of the invention has been explained below in Sections (a) though (g).

(a) Test Methods

The standard test methods for unconsolidated-undrained triaxial (UU) compression test and consolidated undrained (CU) triaxial compression test for cohesive soils are described in ASTM Designation: D2850-03a (reapproved 2007) and ASTM Designation: D4767-11, respectively. International and national organizations of several countries have their own standards.

UU tests are performed to determine strength and stress-strain relationships of a cylindrical specimen of either undisturbed or remolded cohesive soil. Specimens are subjected to a confining fluid pressure in a triaxial chamber. No drainage of the specimen is permitted during the test. The specimen is sheared in compression without drainage at a constant rate of axial deformation (strain controlled).

CU tests are performed to determine strength and stress-strain relationships of a cylindrical specimen of either an intact, reconstituted, or remolded saturated cohesive soil. Specimen are isotropically consolidated and sheared in compression without drainage at a constant rate of axial deformation (strain controlled).

Triaxial compression tests on cohesionless soils are similarly performed either on dry or partially saturated or fully saturated cylindrical specimen generally with drainage permitted. The specimen is sheared in compression at a constant rate of axial deformation (strain controlled).

(b) Existing Research

One of the main criticisms of triaxial test is the non-uniformity of stress and deformation at all but very small strains (Rowe and Barden, 1964). The main cause of this uniformity is the friction at the end platens, which causes both the barreling effect and the concentration of dilation in local zones, which results in premature development of a failure surface. These disadvantages to some extent are largely overcome the use of lubricated end platens, which by removing the dead zones, allow the use of short samples (Rowe and Barden, 1964). Other causes are insufficient drainage, inherent non-uniformity of soil sample through its height, membrane effects and self-weight (Sheng et. al. 1997). Question arises; how much effect does such non-uniformity have on strength, stress strain characteristics, and volume change characteristics determined from a triaxial test. Different researchers have reached different conclusions (Lee,. 1978). The experimental results indicate that (i) comparison between lubricated and non-lubricated ends, shows that the end friction had little influence on measured internal friction of sand samples (Bishop and Green, 1965), (ii) the end restraint has a significant influence on undrained shear strength of sand, but slight effects on drained strength and on the internal friction angle (Lee, 1978), and (iii) the undrained strength of a dense sand tested with lubricated ends was 20% greater than that with regular ends. Saada and Townsend (1981) summarized theoretical elastic solutions of stress distributions at end platens, and found that the vertical stress at the ends of specimen decreases from a very high concentration at the edge to a lower value at the center, and there are no unique patterns for distributions of radial, circumferential and shear stresses at the ends.

(c) Cross-Sectional Area for a Given Load

Rubber membrane is used to encase the specimen to provide reliable protection against leakage and also for separation between soil specimen and the chamber fluid. The membrane provides insignificant restraint to the specimen. The membrane is sealed to the specimen cap and base with rubber O-rings. The magnitude of fluid pressure in the chamber is selected based on the insitu horizontal pressure that may exist at a selected depth for which test is being performed to determine strength, stress-strain relationship and volume change characteristics. The fluid pressure cannot restrain the cylindrical soil specimen to maintain the uniform diameter through its height during shear, due to (1) end restraint imposed by the specimen end platens and (2) inherent non-uniformity in soil. With the result that soil specimen deforms laterally, but non-uniformly as shown in FIG. 1(b). The cross-sectional area, A, for a given applied load, is based on the assumption that the specimen deforms as a right circular cylinder with constant diameter during shear (Rochelle et al., 1988). With this assumption, A for a given applied load at an instant of time t, is given by:

$$A = \frac{A_c}{(1-\varepsilon_v)} \quad (1)$$

Where:
$A_c$=Average cross-sectional area of the specimen after consolidation and before beginning the test.
$\varepsilon_v$=Axial strain for the given axial load at any instant time t=$\Delta H/H$
$\Delta H$=Change in height of specimen during loading
H=height of specimen after consolidation.
D=Diameter of specimen after consolidation.

When specimen fails or deforms by bulging with no apparent shear plane, it is generally agreed that cross-sectional area, A, is given by:

$$A = A_c \frac{1+\frac{\Delta V}{V}}{1-\varepsilon_v} \quad (2)$$

It may be noted that the cross-sectional area which may govern the value of deviator stress may be controlled by the area at a height where the shearing is more intense and where slip plane may form and not necessarily by average value, A, calculated by Eqs. 1 and 2. Non-uniform stress conditions within the test specimen are imposed by the specimen end platens. This can also cause redistribution of void ratio within the specimen causing non-uniformity in the soil specimen during the test. In these conditions, it remains unknown as to what could have been the volume change characteristics (such as decrease in volume or increase in volume known as dilation) of the soil specimen any time during shear or at failure or at peak strength, had non-uniform lateral displacement and non-uniform stress conditions not taken place, i.e. uniform lateral displacement had occurred through its height. The non-uniform lateral displacement is generally attributed to end area effect imposed by specimen end platens, and also because the fluid pressure in chamber cannot restrain or provide enough lateral stiffness to the specimen to maintain the same diameter of the specimen through its height. In the above mentioned conditions, the specimen, which was cylindrical in shape in the beginning of the test, becomes barrel shape during the process of shearing.

(d) Expandable Jacket

The expandable jacket has been designed to expand uniformly through its height, which thereby allows only uniform lateral displacement of the specimen during the triaxial compression test. The expandable jacket shall not permit the cylindrical specimen to develop a barrel shape or develop localized bulging during the test. Even if there is some or little inherent non-uniformity of void ratio in the real soil specimen, the expandable jacket will maintain its uniform diameter. In insitu stress conditions, uniform lateral stiffness or confinement is provided to a soil element by the soil around it and so, when the soil element is axially loaded, it experiences vertical displacement along with uniform lateral displacement. The uniform lateral resistance in insitu conditions does not allow non-uniform lateral displacement to occur. This type of confinement is not provided by fluid pressure in a triaxial cell. The end effects at top and bottom porous discs and end platens, creates non-uniform lateral displacement which cannot be prevented by fluid pressure.

Spherical and cavity expansion theories have been applied to analyze the cone penetration problems and also pile tip load at failure with the assumption that the cone penetration or pile tip penetration simulates cylindrical or spherical cavity expansion in soil (Vesic, 1972, Gupta, 2002a and 2002b). The triaxial compression test with expandable jacket around the soil specimen shall impose the same conditions as are expected to occur in soil when cone penetration or progressive pile penetration occurs with increase in load.

FIG. 1(a) shows the initial cylindrical shape of soil specimen with uniform diameter through its height before the beginning of the triaxial compression test, i.e., before consolidation. FIG. 1(b) shows that non-uniform lateral displacement of specimen occurs progressively during the test and forms a barrel shape (sometimes even with localized bulging). The main objective of this invention is to prevent non-uniform displacement or localized bulging by use of an expandable jacket, which has been designed to maintain uniform lateral displacement of soil specimen through its height during the test.

Figure 2:
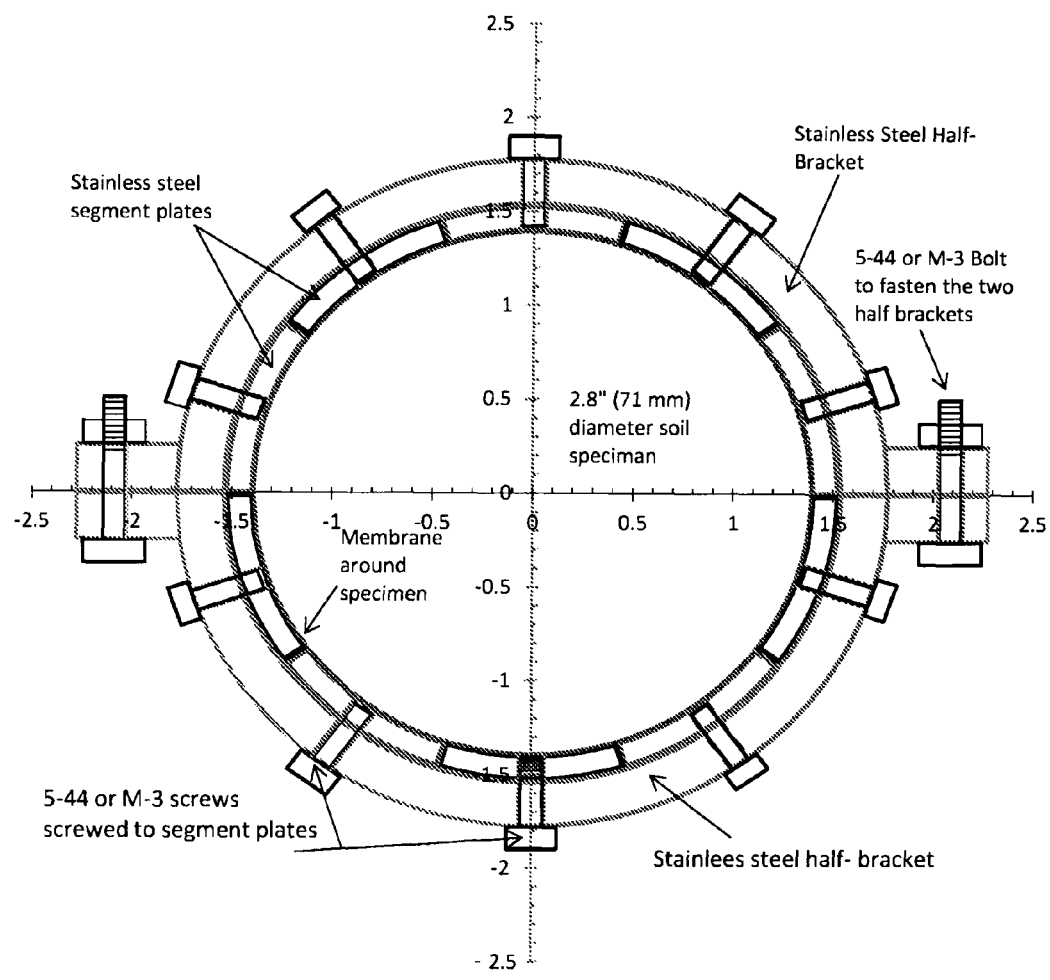
FIG. 2 describes the plan view of the segment circular stainless steel plates assembled in position with the help of two half-brackets.
Figure 3:
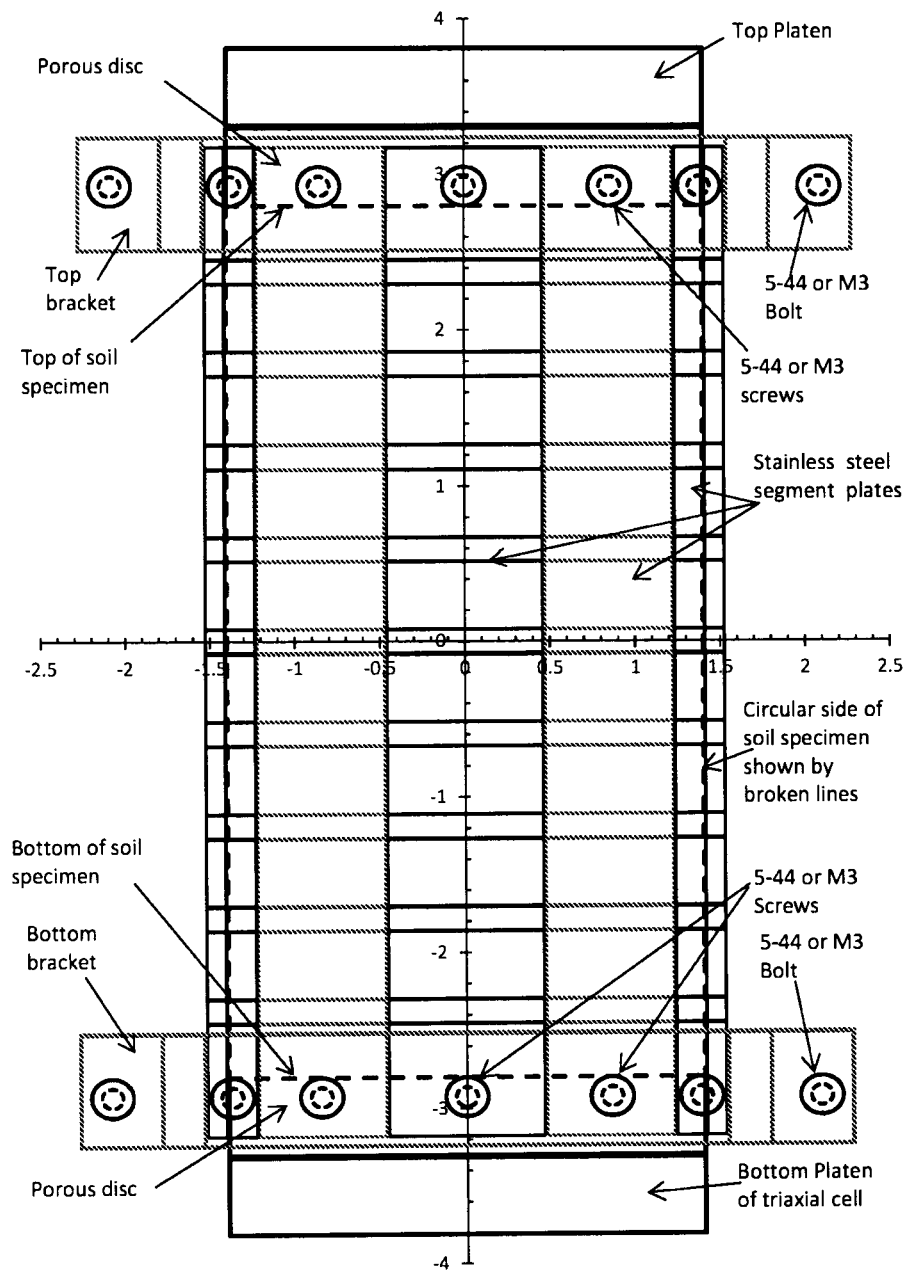
FIG. 3 describes the elevation of view of the segment circular stainless steel plates assembled in position with the help of two half-brackets.
Figure 4:
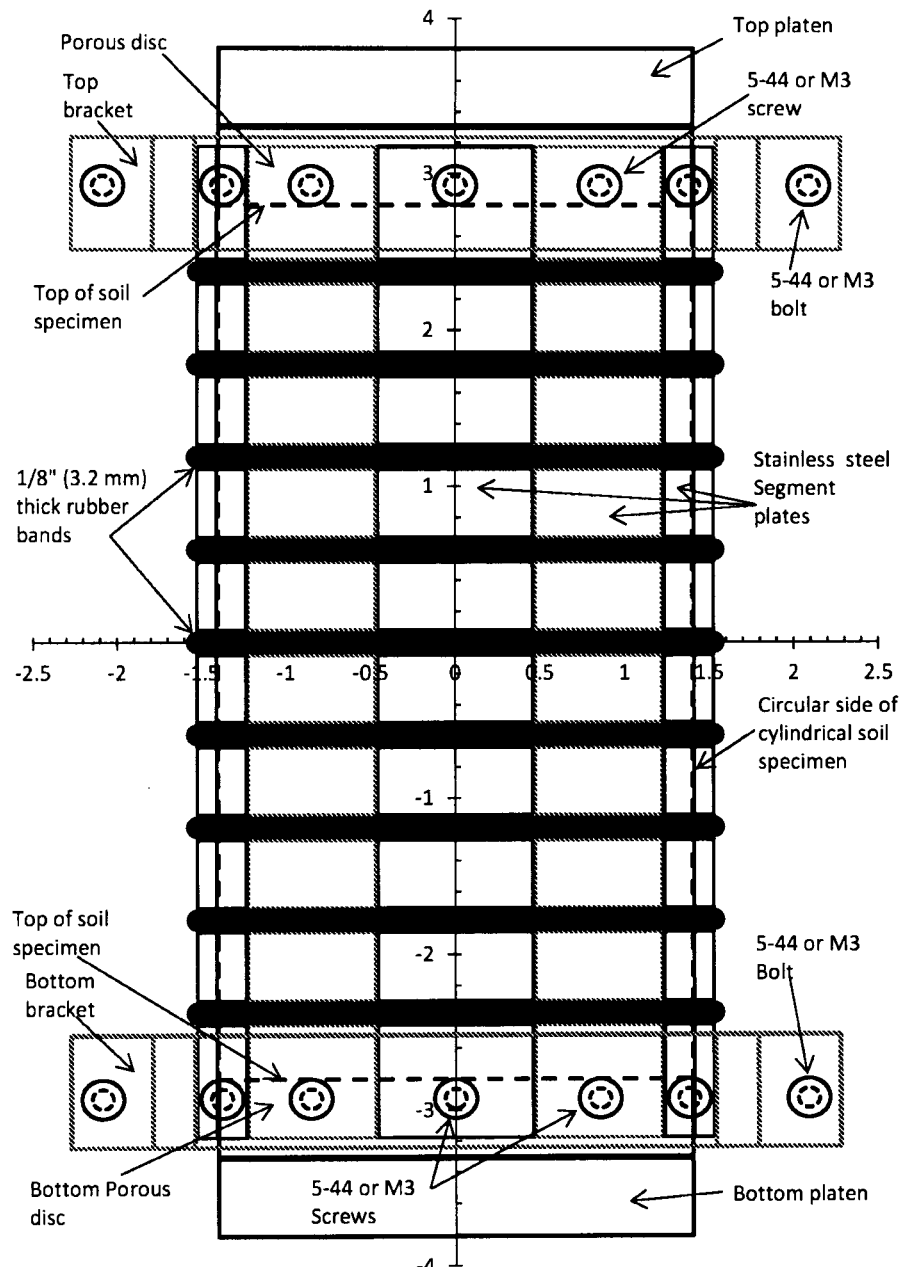
FIG. 4 shows the elevation view, when rubber bands of minimum ⅛" (3.2 mm) thickness has been slipped on around the segmental plates.
Figure 5:
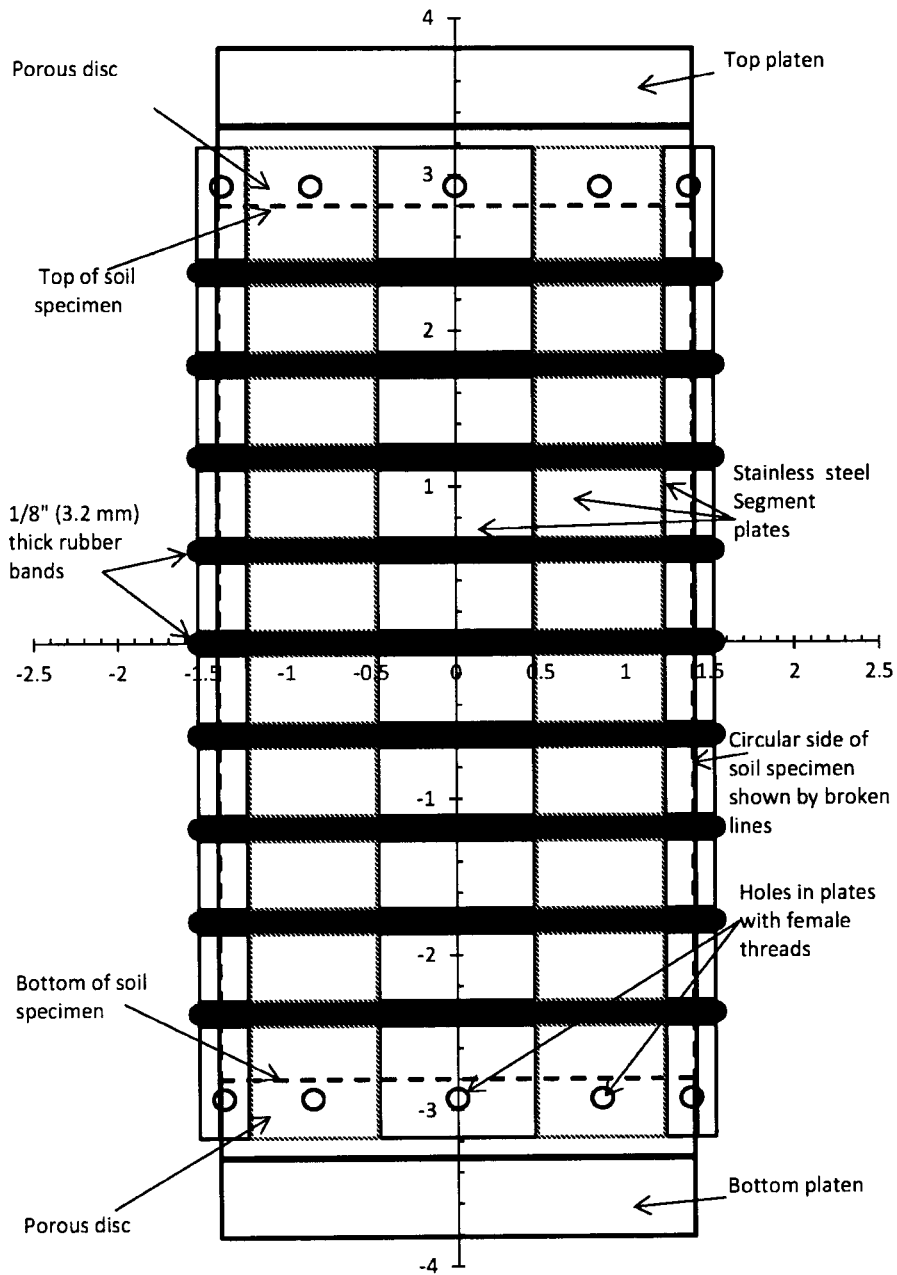
FIG. 5 shows that the two half brackets have been uninstalled and the rubber bands in the space previously occupied by half-brackets have also been slipped around segment plates.

The expandable jacket consists of about 10 stainless steel segment plates, circular arch in shape for 2.8" (71 mm) diameter specimen as shown in FIG. 2. The thickness of plates may vary between ⅛" and ⅜" (3.2 mm and 9.53 mm) in thickness. Thicker segmental will not bend under the force exerted by rubber bands and in this respect may have some advantage over thinner plates. These plates are installed around the membrane which covers the specimen, using two-half circular brackets as shown in FIG. 2 and FIG. 3. The thickness of these brackets can vary between ¼" and ⅜" (6.35 mm and 9.53 mm). Rubber bands of minimum ⅛" (3.2 mm) thickness are slipped on around the plates at marked locations as shown in FIG. 4. The width of rubber bands can vary between ⅛" and ⅜" (3.2 mm and 9.53 mm). The upper and lower brackets are then un-installed. Remaining rubber bands are slipped on around the plates in the space earlier covered by the brackets, as shown in FIG. 5. The expandable jacket has thus been installed around the soil specimen. Since segmental circular plates are resting against the top and bottom porous discs, initially the lateral load exerted by rubber bands acts on the porous discs and very little, if any, directly on the soil specimen in the beginning of the test. When specimen begins to undergo lateral displacement or lateral expansion under the vertical load applied on the specimen during test, the rubber bands around the segmental plates shall stretch and exert pressure on the segmental plates thereby on the surface of the soil specimen all along its height and shall help in maintaining the uniform diameter through its height during the test, the plates are then not in contact with porous discs and so rubber bands exerts lateral pressure on the specimen. As many rubber bands as needed to maintain uniform diameter of cylindrical specimen, shall be used. The inside surface of segment plates shall be lubricated to reduce friction between rubber membrane around soil specimen and the plates. The function of segmental stainless steel plates is to uniformly distribute the lateral load applied by rubber bands on the soil specimen.

Figure 6:
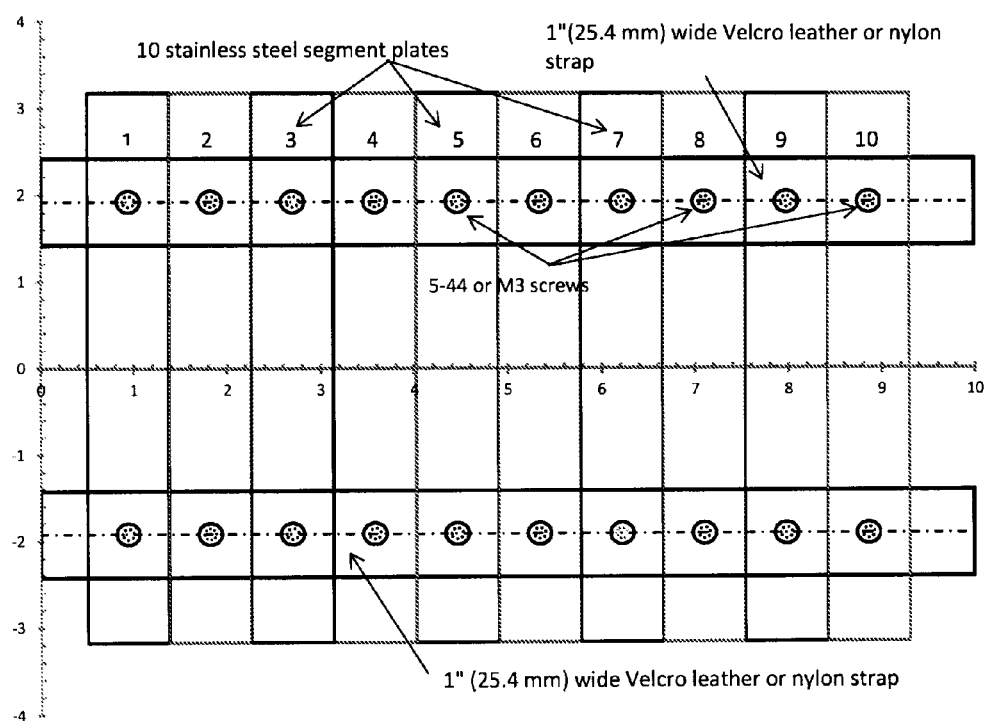
FIG. 6 shows alternative method of installing segment plates using two leather or nylon or poly-propylene VELCRO straps. In this method, segment plates are first assembled by screwing them through VELCRO straps.
Figure 7:
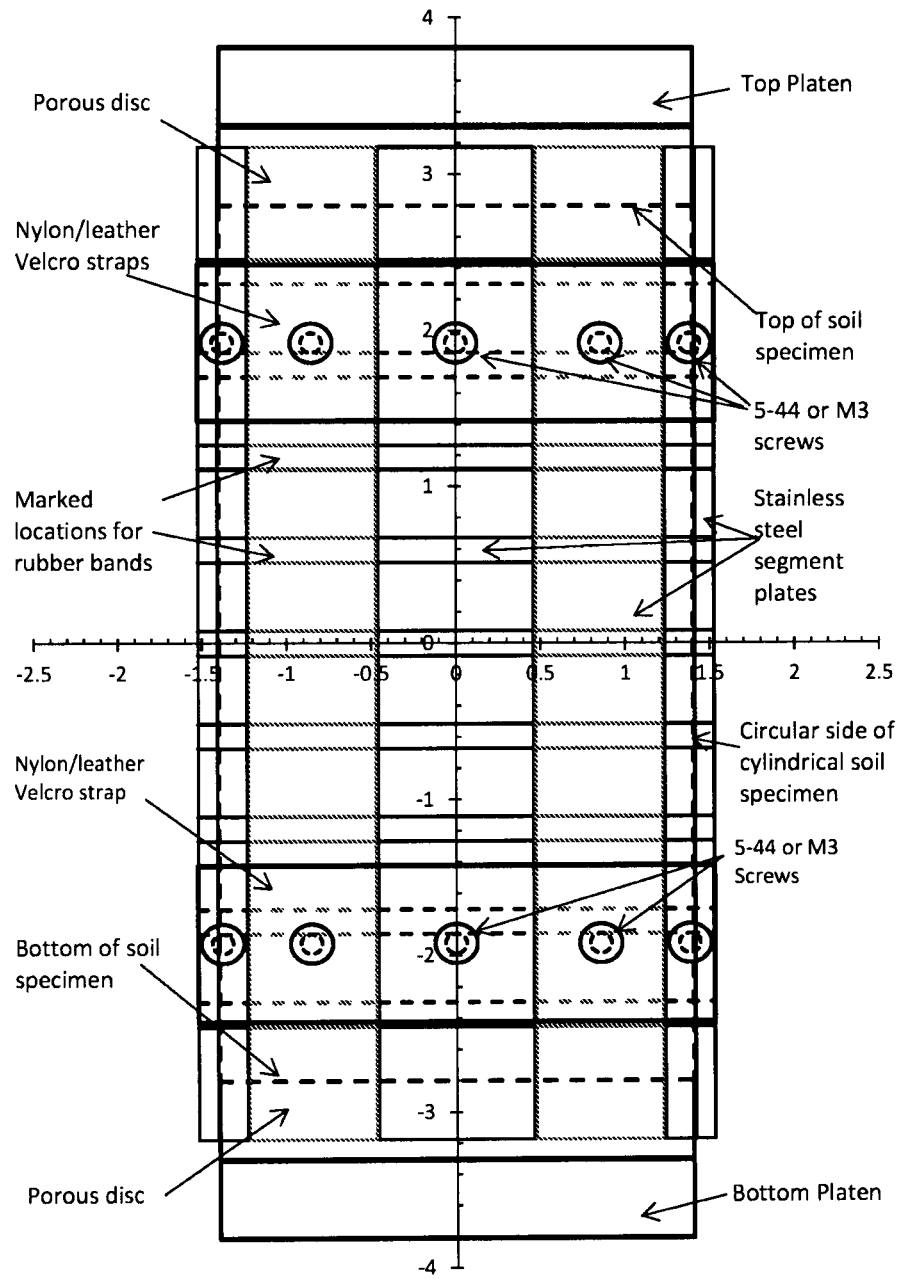
FIG. 7 shows that the segment plates have been wrapped around soil specimen.
Figure 8:
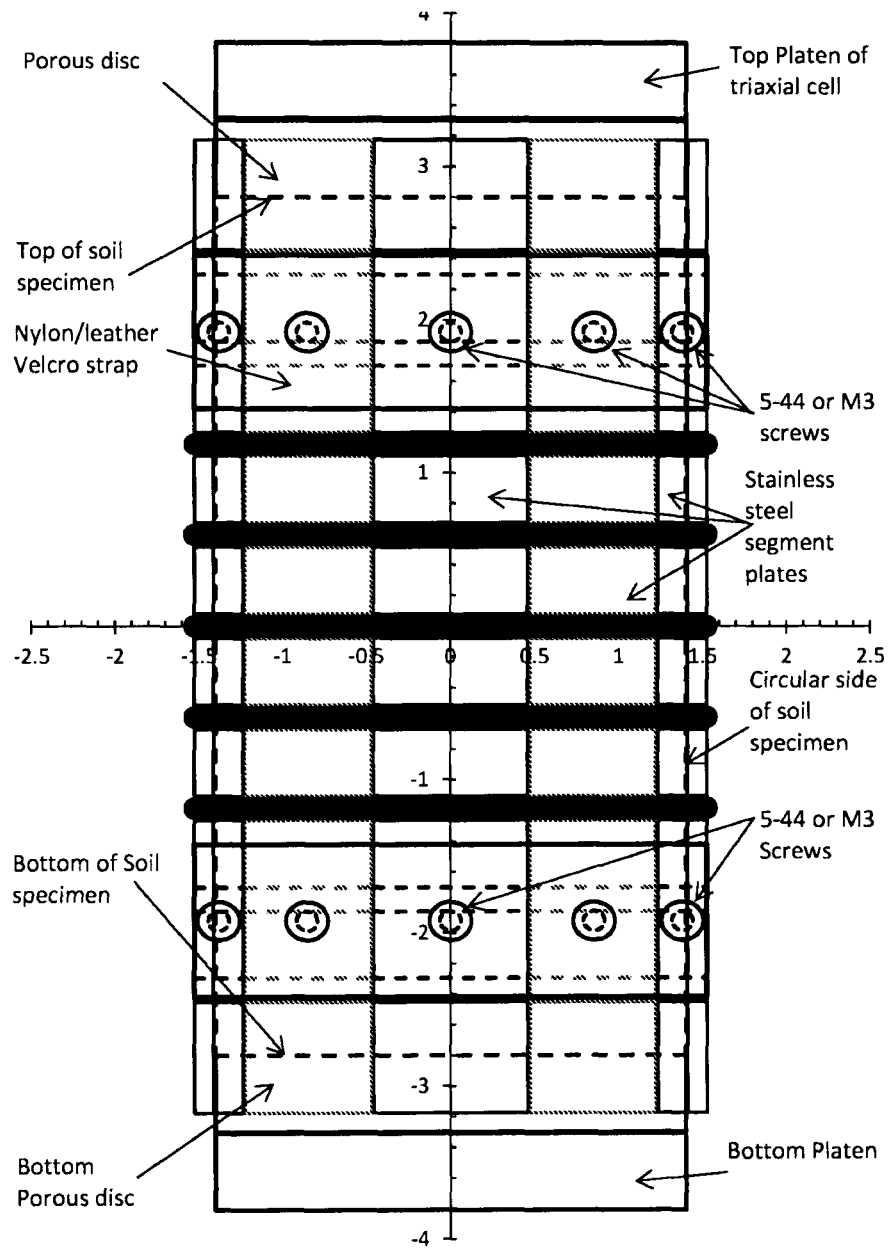
FIG. 8 shows that the rubber bands have been slipped on around the segment plates.
Figure 9:
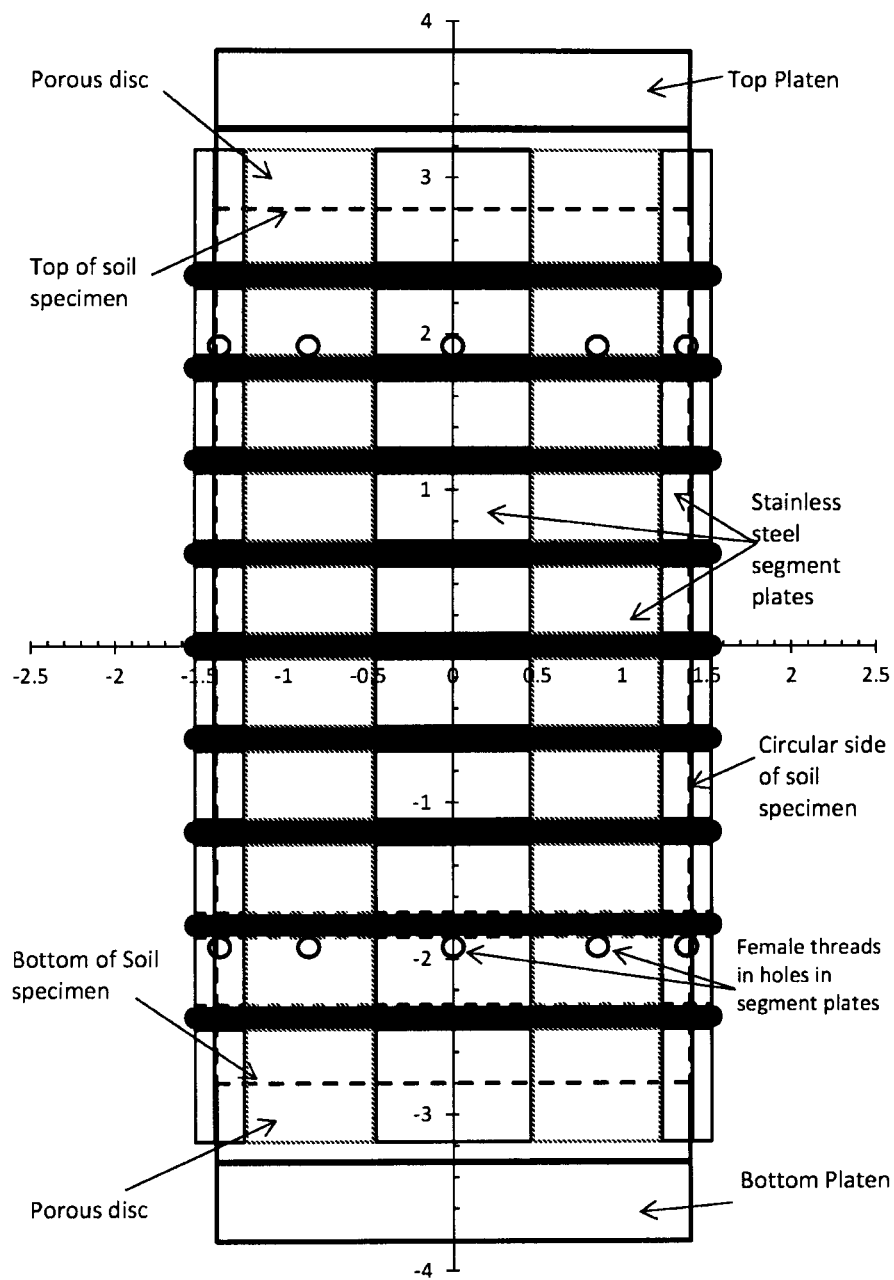
FIG. 9 shows that VELCRO straps have been uninstalled after un-screwing those screws, which attached the VELCRO straps to segment plates. Additional rubber bands are slipped on around the segment plates previously occupied by VELCRO straps.

Alternatively, the lubricated segment plates can be assembled around soil specimen by use of two 1" (25.4 mm) wide leather or nylon or polyester or polypropylene VELCRO straps. First, segment plates are fastened to VELCRO strap using 5-44 or M-3 screws as shown in FIG. 6 (other screw sizes may be used along with appropriate female threads in segment plates). Then the assembled plates are wrapped around the soil specimen and maintained in position by Velcro strap as shown in FIG. 7. The rubber bands of minimum thickness of ⅛" (3.17 mm) are slipped on around the plates as shown in FIG. 8. The screws are unthreaded to remove the straps. The remaining rubber bands are then slipped on around the plates in the space earlier occupied by the VELCRO straps, as shown in FIG. 9. The expandable jacket has now been installed around the soil specimen. The other steps such as placing the chamber, filling the chamber with water and installing loading device on top platen etc are followed as per ASTM standards to perform the triaxial compression test.

Sizes of segment plates, half brackets and rubber bands shown in FIG. 2 through FIG. 9 and described in the text above are based on soil specimen diameter of 2.8" (71 mm) in diameter. Diameter of soil specimen generally used, are 2.8" (71 mm) or 4" (100 mm). Diameter of soil specimen is also dependent on inside diameter of Shelby tubes. Inside diameter of Shelby tubes as per ASTM standards are 1.905" (48.42 mm), 2.87" (72.9 mm) and 4.76" (120.9 mm). The diameter of circular arch shaped segment plates and two half brackets shall depend on the diameter soil specimen. Number of segment plates shall be 8, 10 and 16 for soil specimen of 1.905" (48.42 mm), 2.87" (72.9 mm) and 4.76" (120.9 mm), respectively. For other specimen sizes, special design detail shall be used.

Figure 10:
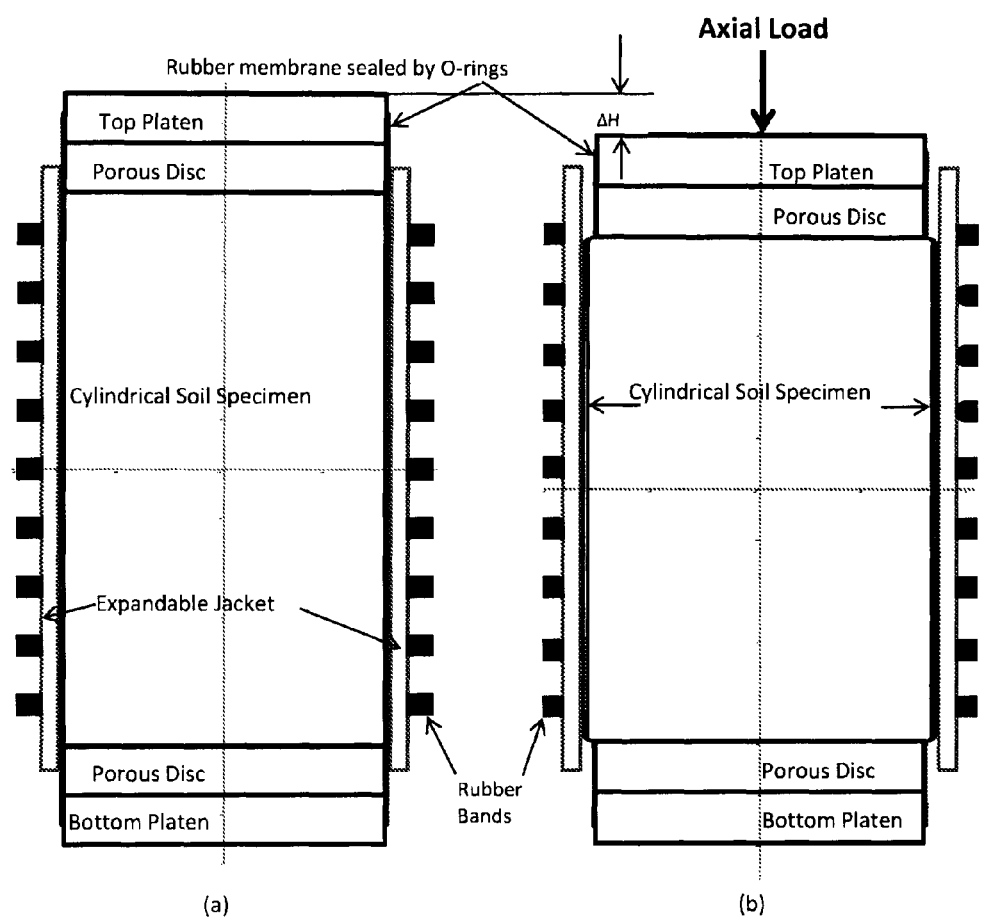
FIG. 10 has been drawn to show that because of expandable device, soil specimen undergoes uniform lateral displacement with cylindrical shape during the test.

As described above, the expandable jacket shall maintain cylindrical shape of the soil specimen and its diameter shall remain uniform through its height during the test as shown in FIG. 10. Near the bottom and top porous disc, the diameter of specimen shall transition from diameter of porous disc to expanded diameter of the specimen as shown in FIG. 10. Height of the transition shall be expected to be about two times of the increase in radius of soil specimen as load distribution occurs at 1H:2V in accordance with accepted theories. Calculations for height of transition shown in Table 1 for sand with Poisson's ratio of 0.3 and Table 2 for saturated clay with Poisson's ratio of 0.5, are applicable for below top porous disc and also above the bottom porous disc. As per these calculations, the height of transition is very small and varies from 0.042" (1 mm) to 0.14" (3.6 mm) for axial strains between 1 and 10%. Though remaining height, the expandable jacket shall succeed in maintaining cylindrical shape with uniform diameter.

The lateral stress exerted by the rubber membrane and rubber bands around cylindrical soil specimen for various values of axial strain is also calculated in Tables 1 and 2. The lateral stress exerted by rubber bands and membrane shall be a product of lateral strain and modulus of elasticity of rubber.

As shown in Table 1, the lateral stress, exerted by rubber membrane and rubber bands on soil specimen, varies from 0.3 psi at 1% axial strain to 4.5 psi at 15% axial strain for sand specimen with Poisson's ratio of 0.3. As shown in Table 2, the lateral stress exerted by rubber membrane and rubber bands varies from 0.5 psi at 1% axial strain to 7.5 psi at 15% axial strain for saturated clay specimen with Poisson's ratio of 0.5. These calculations are based on assumed value of E of rubber equal to 100 psi. Thus not only expandable jacket helps to maintain cylindrical shape with uniform diameter but also helps to quantify the lateral stress exerted by rubber bands and membrane accurately. Note: 1 psi=6.894757 kN/m$^2$, 1"=25.4 mm, 1 ft=0.3048 m. If considered necessary for research purposes or for other routine testing, LVDT devices for measuring lateral expansion of specimen or uniform increase in diameter during the test can be used.

TABLE 1

Calculations for lateral stress exerted by rubber bands during the test for sand specimen with Poisson's ratio of 0.3, H = 5.6", d = 2.8", E of Rubber = 100 psi.

| Axial Strain ($\epsilon_v$) = ($\Delta$H/H) * 100 % | Axial Displacement ($\Delta$H) = $\epsilon_v$ * H/100 inches | Lateral Strain ($\epsilon_l$) = v * $\epsilon_v$ % | Increase in radius of specimen, $\Delta$r inches | Height near ends in which load distribution shall occur, $\Delta$h = 2 * $\Delta$r inches | Lateral stress exerted by rubber bands and membrane = E * $\epsilon_l$ psi |
|---|---|---|---|---|---|
| 1 | 0.056 | 0.3 | 0.0042 | 0.0084 | 0.3 |
| 2 | 0.112 | 0.6 | 0.0084 | 0.0168 | 0.6 |
| 3 | 0.168 | 0.9 | 0.0126 | 0.0252 | 0.9 |
| 4 | 0.224 | 1.2 | 0.0168 | 0.0336 | 1.2 |
| 5 | 0.28 | 1.5 | 0.021 | 0.042 | 1.5 |
| 6 | 0.336 | 1.8 | 0.0252 | 0.0504 | 1.8 |
| 7 | 0.392 | 2.1 | 0.0294 | 0.0588 | 2.1 |
| 8 | 0.448 | 2.4 | 0.0336 | 0.0672 | 2.4 |
| 9 | 0.504 | 2.7 | 0.0378 | 0.0756 | 2.7 |
| 10 | 0.56 | 3 | 0.042 | 0.084 | 3 |
| 15 | 0.84 | 4.5 | 0.063 | 0.126 | 4.5 |
| 20 | 1.12 | 6 | 0.084 | 0.168 | 6 |

TABLE 2

Calculations for lateral stress exerted by rubber bands during the test for specimen of saturated clay with Poisson's ratio of 0.5, H = 5.6", d = 2.8", E = 100 psi.

| Axial Strain ($\epsilon_v$) = ($\Delta$H/H) * 100 % | Axial Displacement ($\Delta$H) = $\epsilon_v$ * H/100 inches | Lateral Strain ($\epsilon_l$) = v * $\epsilon_v$ % | Increase in radius of specimen, $\Delta$r inches | Height near ends in which load distribution shall occur, $\Delta$h = 2 * $\Delta$r inches | Lateral stress exerted by rubber bands and membrane = E * $\epsilon_l$ psi |
|---|---|---|---|---|---|
| 1 | 0.056 | 0.5 | 0.007 | 0.014 | 0.5 |
| 2 | 0.112 | 1 | 0.014 | 0.028 | 1 |
| 3 | 0.168 | 1.5 | 0.021 | 0.042 | 1.5 |

TABLE 2-continued

Calculations for lateral stress exerted by rubber bands during the test for specimen of saturated clay with Poisson's ratio of 0.5, H = 5.6", d = 2.8", E = 100 psi.

| Axial Strain ($\epsilon_v$) = ($\Delta$H/H) * 100 % | Axial Displacement ($\Delta$H) = $\epsilon_v$ * H/100 inches | Lateral Strain ($\epsilon_l$) = v * $\epsilon_v$ % | Increase in radius of specimen, $\Delta$r inches | Height near ends in which load distribution shall occur, $\Delta$h = 2 * $\Delta$r inches | Lateral stress exerted by rubber bands and membrane = E * $\epsilon_l$ psi |
|---|---|---|---|---|---|
| 4 | 0.224 | 2 | 0.028 | 0.056 | 2 |
| 5 | 0.28 | 2.5 | 0.035 | 0.07 | 2.5 |
| 6 | 0.336 | 3 | 0.042 | 0.084 | 3 |
| 7 | 0.392 | 3.5 | 0.049 | 0.098 | 3.5 |
| 8 | 0.448 | 4 | 0.056 | 0.112 | 4 |
| 9 | 0.504 | 4.5 | 0.063 | 0.126 | 4.5 |
| 10 | 0.56 | 5 | 0.07 | 0.14 | 5 |
| 15 | 0.84 | 7.5 | 0.105 | 0.21 | 7.5 |
| 20 | 1.12 | 10 | 0.14 | 0.28 | 10 |

(e) Correction for Rubber Bands Using Existing Methods

ASTM Designation D4767-11 and ASTM Designation D2850-03 (Reapproved 2007) describe the correction for rubber membrane. Similar type of correction shall be applied to correct the principal stress difference (deviator stress) for the effect of the rubber bands used in expandable jacket:

$$\Delta(\sigma_1 - \sigma_3)_{rm} = \frac{(4 E_{rb}\, T_{rb}\, \varepsilon_1)}{D} \quad (3)$$

Where:
$\Delta(\sigma_1-\sigma_3)_{rb}$=rubber band correction to be subtracted from the measured principal stress difference (deviator stress),
$E_{rb}$=Young's modulus for the rubber band material,
$T_{rb}$=Equivalent thickness of the rubber bands for correction=$(n\, t_{rb}\, b)/H$
$t_{rb}$=thickness of rubber bands,
b=width of rubber bands,
n=number of rubber bands used around segmental plates,
$\Sigma_1$=axial strain,
H=Height of soil specimen,
D=diameter of specimen after consolidation=$(4\, A_o/\pi)^{0.5}$ (f) Correction for Rubber Bands Using a Specially Designed Calibration Device Expandable jacket shall expand during the test, and the rubber bands shall provide the lateral force on the soil specimen. The magnitude of lateral force is a product of modulus of elasticity and lateral strain experienced by rubber bands.

Figure 11:
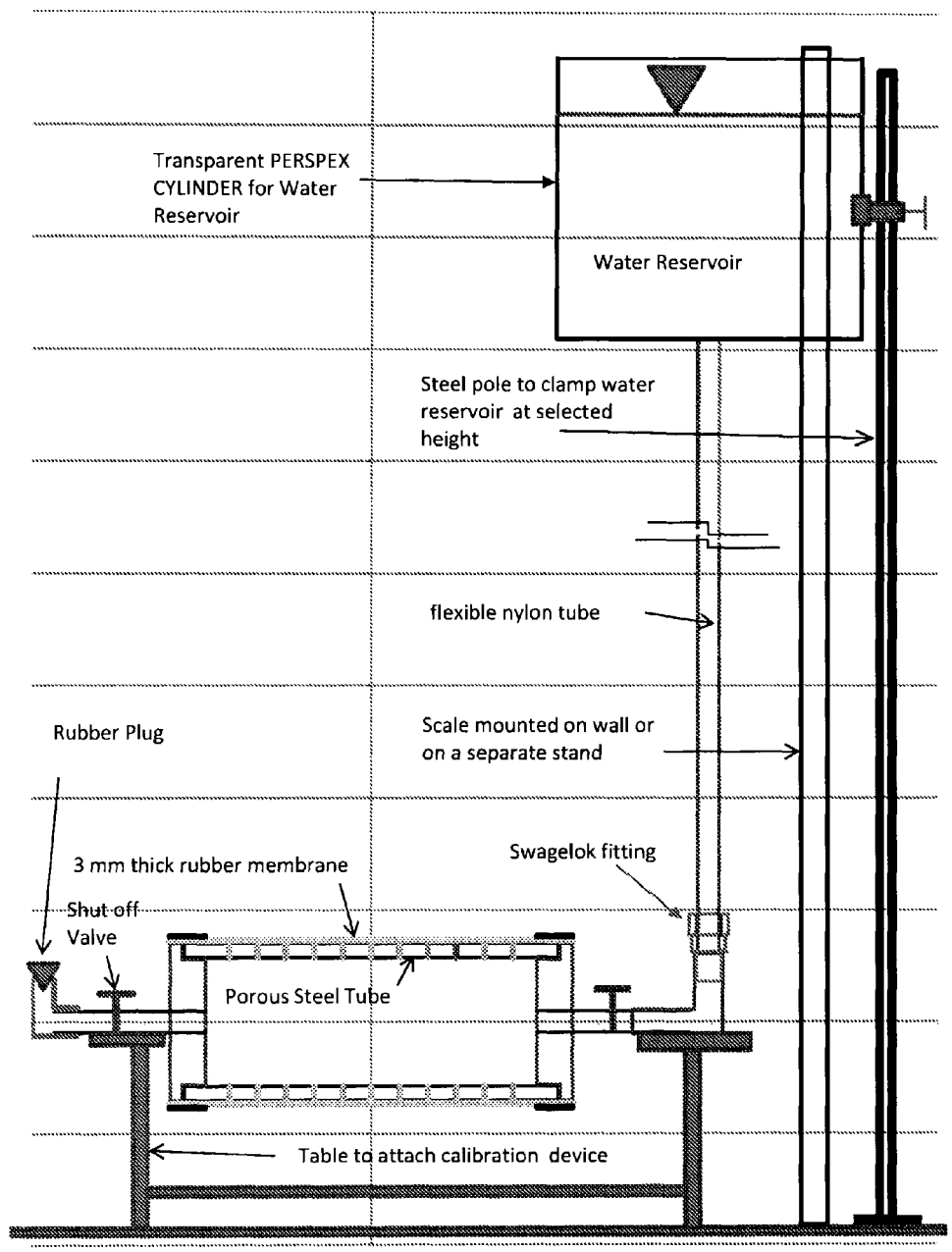
FIG. 11 shows the calibration device.
Figure 12:
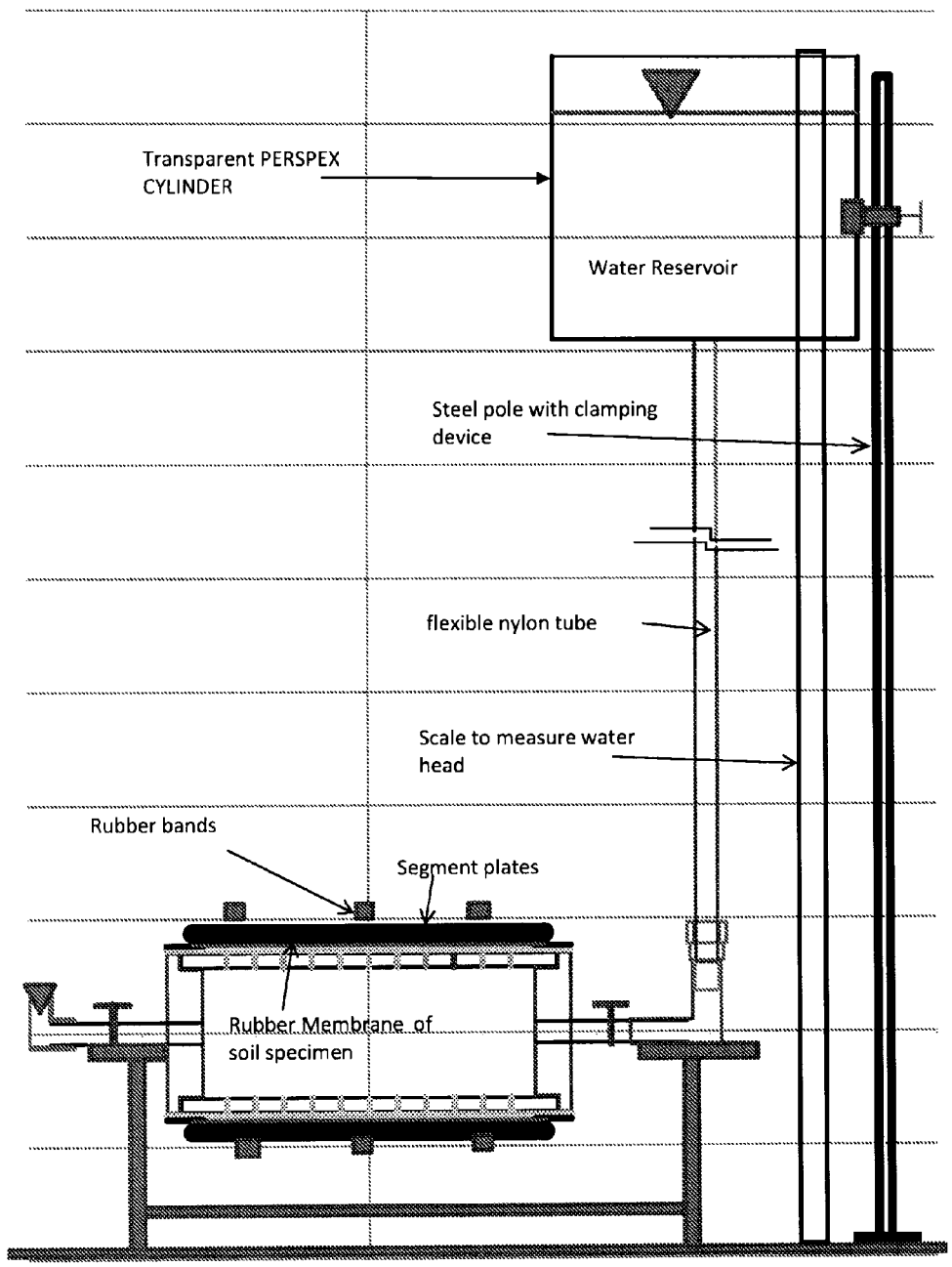
FIG. 12 shows that expandable jacket has been installed on calibration device to perform calibration of the expandable jacket.

A calibration device as shown in FIG. 11 and FIG. 12 shall be used to provide the data for the magnitude of correction required for deviator stress at various level of lateral strain during the test. The PERSPEX or clear acrylic made of polymethyl methacrylate cylindrical reservoir, 4" to 12" (100 and 300 mm) in diameter, shall be raised by a foot (0.3 m) each time to expand the calibration device as shown in FIG. 11 and also on expandable jacket mounted on calibration device as shown in FIG. 12 to provide data of water head on calibration device and change in volume of water flowing from reservoir to calibration device. The reservoir can be raised to any height varying between 2 and 8 ft (0.6 and 2.4 m). If ceiling height of laboratory is more than 10 ft (3.28 m), then necessary arrangements shall be made for raising reservoir for water head greater than 8 ft (2.4 m). Graduated scale shall have graduations nearest to 0.01 ft on one edge and 3 mm on the other edge with or without a vernier gage.

The calibration device consists of a porous stainless steel tube with end caps sealed for water tightness. 3 mil thick rubber membrane is mounted on porous stainless steel tube. The rubber membrane is clamped at the ends of porous stainless steel tube for water tightness. On one end, a brass tube shall outlet the porous stainless steel tube to remove the air bubbles from water when water is filled in the porous steel tube. When air bubbles are not seen coming out from the tube, the valve shall be closed. The brass tube on the other end of the porous stainless steel tube shall lead towards water reservoir. The reservoir shall be connected to a flexible and transparent nylon tube. On the lower end, the nylon tube connects to the porous stainless tube through Swagelok fitting to brass tube for water tightness.

The calibration of the calibration device as shown in FIG. 11 shall be first done and data recorded in Table 3 (a). Thereafter, the rubber membrane, (same as to be used for the soil specimen), shall be mounted on 3 mil (mm) thick rubber membrane. The expandable jacket shall be mounted on the rubber membrane with the help of half-brackets or Velcro straps as previously detailed in FIG. 2 through FIG. 10. The calibration of the expandable device shall be done raising reservoir for every a foot (0.3048 m). The calibration data shall be recorded in Table 3 (b). The lateral stress exerted by 3 ml thick rubber membrane shall be deducted from the lateral stress exerted by calibration device plus the 3 ml thick rubber membrane to determine the correct value of lateral stress exerted by expandable device on the soil specimen at various levels of lateral strain during the test.

During the triaxial compression test, new diameter of 100% water saturated soil specimen at any instant of time shall be calculated based on the measured reading of axial displacement and volume of flowing out of soil specimen. For dry soil specimen, the new diameter shall be calculated approximately using Eq. 1. Eq. 1 does not take reduction or increase in void ratio which occurs during the triaxial compression test. The value of correction in the value of deviator stress shall depend on the value of lateral strain of rubber bands at an instant of time, during the test. The lateral strain of rubber bands shall depend on change in diameter of soil specimen. Based on the value of lateral strain, the correction in deviator stress shall be calculated and applied to the deviator stress and then used for analyzing the triaxial test data to determine shear strength, stress-strain relationship and volume change characteristics.

(g) Conclusions

The invention of expandable jacket included in this claim shall maintain cylindrical shape of the soil specimen during the triaxial compression test. For more than 100 years, the main criticism of triaxial compression test has been that the cylindrical shape becomes barrel shape with localized bulging during the test. With the invention of expandable jacket as included in this claim, this more than 100 year old criticism, which has not been resolved so far, shall be completely overcome and the cylindrical shape of the specimen with uniform diameter shall be maintained as is necessary to perform an accurate triaxial test. The calibration device as included also in this claim shall accurately quantify the additional lateral stress exerted by the expandable jacket on the cylindrical soil specimen during the test and help in applying accurate correction to deviator stress.

TABLE 3 (a)

Form for entering data to calibrate the calibration device

| Serial No. | Height of Water Level in Reservoir above Centerline of Porous Stainless steel Tube (ft or m) | Water Level in Reservoir (inch or mm) | Drop ($\Delta h$) in Level of Reservoir (inch or mm) | Increase in Diameter of membrane, $\Delta d$ (inch or mm) | Lateral Strain, $\epsilon_l$ = $\Delta d/d$ | Water Pressure ($p_w$) in psi (kg/mm$^2$) | Modulus of Elasticity (E) of rubber in psi or kg/mm$^2$ |
|---|---|---|---|---|---|---|---|
| | 0.5 ft (0.150 m) | ... | | | | | |
| | 1 ft (0.305 m) | ... | ... | ... | ... | ... | ... |
| | 2 ft (0.61 m) | | | | | | |
| | 3 ft (0.914 m) | | | | | | |
| | 4 ft (1.219 m) | | | | | | |
| | 5 ft (1.524 m) | | | | | | |
| | 6 ft (1.829 m) | | | | | | |
| | 7 ft (2.134 m) | | | | | | |
| | 8 ft (2.438 m) | | | | | | |
| | 9 ft (2.743 m) | | | | | | |
| | 10 ft (3.048 m) | | | | | | |

Outside diameter of porous stainless tube with 3 mil thick rubber membrane, d = ...,
Length of 3 mil thick rubber membrane between end clamps, L = ...
Cross-sectional Area of device, A = $\pi d^2/4$, Volume of device = A * L
Inside diameter of reservoir = $d_r$, Cross-sectional Area of reservoir, $A_r$ = $\pi d_r^2/4$
Increase in Diameter of device, $\Delta d$, after raising reservoir = $[(d^2 + 4 * A_h * \Delta h/(\pi * L)]^{0.5} - d$
E of rubber membrane = $pw/\epsilon_l$

REFERENCES

Bishop, A. W. and Green, G. E. (1965). "The influence of end restraint on the compression strength of a cohesionless soil," *Geotechnique*, Vol. 15, pp. 243-266.

Gupta, R. C. (2002 a). "Finite strain analysis for expansion of cavities in granular soils," *Soils and Foundations*, Vol. 42, No. 6, pp. 105-115.

Gupta, R. C. (2002 b). "Estimating bearing capacity factors and cone tip resistance," *Soils and foundations*, Vol. 42, no. 6, pp. 117-127.

Lee, K. L. (1978). "End restraint effects on undrained static triaxial strength of sand," *Journal of Geotechnical Engineering Division*, Vol. 104, pp. 687-703.

Rochelle, P. L., Leroueil, S., Trak, B., Blais-Lerox, L., and Tavenas, F. (1988). "Observational approach to membrane and area corrections in triaxial tests," Advanced Triaxial Testing of Soil and Rock, ASTM, STP 977, Eds. R. T. Donaghe, Chaney, R. C., Silver, M. L., ASTM, Philadelphia, pp. 715-731.

Rowe, P. W. and Barden, L. (1964). "Importance of free ends in triaxial testing," *Journal of Soil Mechanics and Foundations Division*, ASCE, Vol. 90, No. SM1, pp. 1-27.

Saada, A. S. and Townsend, F. C. (1981). "Laboratory strength testing of soils, state of the art," *Laboratory Shear Strength of Soil, ASTM*, Special Technical Publication 740, eds. R. N. Yong and F. C. Townsend, ASTM, Philadelphia, pp. 7-77.

Sheng, D, Westerberg, B, Mattsson, H, and Axelsson, K. (1997). "Effects of end restraint and strain rate in triaxial tests," *Computers and Geotechnics, Vol.* 21, No. 3, pp. 163-182.

Vesic, A. S. (1972). "Expansion of cavities in infinite soil mass, "*Journal of Soil Mechanics and Foundation Division*, ASCE, 98(3), pp. 265-290.

The invention claimed is:

1. An expandable jacket and its calibration device:
The expandable jacket comprising;
a. a rubber membrane containing a soil specimen,
b. radially mounted outside the membrane, vertically segmented and axially mounted stainless steel plates, these plates are supported radially by two stainless steel brackets mounted together with bolts, one set of brackets is mounted near the top and one near the bottom of the jacket, the segmented plates and the brackets are attached to each other by screws that penetrate from outside the jacket through the brackets and into the plates,
c. these plates further have elastomeric rubber rings or bands horizontally mounted around the plates,
d. these plates also have nylon or leather straps horizontally mounted with screws around the plates,
e. the bottom of the expandable jacket comprising a bottom platen with a porous disc placed on top of the platen and with the soil specimen resting on the disc,
f. the top of the expandable jacket comprising a top platen with a porous disc placed underneath of the bottom of the platen and with the soil specimen underneath the disc,
g. when the expandable jacket is placed around a soil specimen, the specimen can undergo a uniform radial expansion without bulging as it undergoes a vertical load applied on the specimen during a triaxial compression test with the specimen maintaining its uniform cylindrical shape.

* * * * *